US009980388B2

United States Patent
Tai et al.

(10) Patent No.: US 9,980,388 B2
(45) Date of Patent: May 22, 2018

(54) BIOCOMPATIBLE RIBBON CABLE WITH NARROW FOLDED SECTION

(71) Applicant: California Institute of Technology, Pasadena, CA (US)

(72) Inventors: Yu-Chong Tai, Pasadena, CA (US); Han-Chieh Chang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days. days.

(21) Appl. No.: 14/974,242

(22) Filed: Dec. 18, 2015

(65) Prior Publication Data

US 2016/0105968 A1    Apr. 14, 2016

Related U.S. Application Data

(63) Continuation of application No. PCT/US2014/055462, filed on Sep. 12, 2014.

(60) Provisional application No. 61/878,988, filed on Sep. 17, 2013.

(51) Int. Cl.
*A61N 1/36* (2006.01)
*H05K 1/18* (2006.01)
*A61N 1/05* (2006.01)
*H05K 3/06* (2006.01)

(52) U.S. Cl.
CPC .......... *H05K 1/189* (2013.01); *A61N 1/0543* (2013.01); *A61N 1/36046* (2013.01); *H05K 3/064* (2013.01); *H05K 2201/0154* (2013.01); *H05K 2201/052* (2013.01); *H05K 2201/1003* (2013.01); *H05K 2201/10151* (2013.01)

(58) Field of Classification Search
CPC .. A61N 1/0543; A61N 1/36046; H05K 1/189; H05K 2201/052
See application file for complete search history.

(56) References Cited

U.S. PATENT DOCUMENTS

| 7,774,931 | B2 | 8/2010 | Tai et al. |
| 8,258,909 | B2 | 9/2012 | Li et al. |
| 2008/0064946 | A1 | 3/2008 | Greenberg et al. |
| 2008/0086183 | A1 | 4/2008 | Greenberg et al. |

(Continued)

FOREIGN PATENT DOCUMENTS

EP    3046510    7/2016

OTHER PUBLICATIONS

International Application No. PCT/US2014/55462, International Search Report and Written Opinion dated Sep. 12, 2014, 25 pages.

(Continued)

*Primary Examiner* — Tammie K Heller
(74) *Attorney, Agent, or Firm* — Kilpatrick Townsend & Stockton LLP

(57) ABSTRACT

A biocompatible, micro-fabricated ribbon cable is described in which at least one set of conductors diverges laterally into a bypass wing that forms an aperture through the ribbon cable. The bypass wing is folded in a line through the aperture and over a central portion of the ribbon cable, resulting in a ribbon cable with a narrow, stacked region. The narrow region can fit through small incisions in membranes, such as through an incision in a sclera of an eyeball. The ribbon cable can have an integrally-formed electrode array for attaching to a retina of an eyeball and other electronics for sending signals to the electrode array.

12 Claims, 10 Drawing Sheets

(56) References Cited

U.S. PATENT DOCUMENTS

| | | | |
|---|---|---|---|
| 2008/0221653 A1* | 9/2008 | Agrawal | A61N 1/05 607/118 |
| 2008/0262611 A1 | 10/2008 | Li et al. | |
| 2008/0288036 A1 | 11/2008 | Greenberg et al. | |
| 2012/0192416 A1 | 8/2012 | Neysmith et al. | |
| 2014/0058506 A1 | 2/2014 | Tai et al. | |

OTHER PUBLICATIONS

Chang et al., "High Density 256-Channel Chip Integration with Flexible Parylene Pocket," IEEE, 16th International Solid-State Sensors, Actuators and Microsystems Conference, Jun. 5-9, 2011, pp. 378-381, Beijing, China.

Chang et al., "High Yield Packaging for High-Density Multi-Channel Chip Integration on Flexible Parylene Substrate," IEEE 25th International Conference on, Micro Electro Mechanical Systems, Jan. 29-Feb. 2, 2012, pp. 353-356, Paris, France.

Chang et al., "Reliable Packaging for Parylene-Based Flexible Retinal Implant," 2013 Transducers & Eurosensors XXVII: The 17th International Conference on Solid-State Sensors, Actuators and Microsystems (Transducers & Eurosensors XXVII), Jun. 16-20, 2013, pp. 2612-2615, Barcelona, Spain.

Chen et al., "A 37.6mm2 1024-Channel High-Compliance-Voltage SoC for Epiretinal Prostheses," 2013 IEEE International Solid-State Circuits Conference—Digest of Technical Papers, Feb. 19, 2013, pp. 294-295.

Humayun et al., "Visual Perception in a Blind Subject with a Chronic Microelectronic Retinal Prosthesis," Vision Research, Nov. 2003, pp. 2573-2581, vol. 43, No. 24.

Lin et al., "Creep of Parylene-C Film," IEEE, 16th International Solid-State Sensors, Actuators and Microsystems conference, Jun. 5-9, 2011, pp. 2698-2701, Beijing, China.

Stieglitz, "Development of a Micromachined Epiretinal Vision Prosthesis," J Neural Eng., Dec. 2009, 12 pages, vol. 6, No. 6, IOP Publishing Ltd., United Kingdom.

Theogarajan et al., "Visual Prostheses: Current Progress and Challenges," VLSI Design, Automation and Test, IEEE, International Symposium, Apr. 28-30, 2009, pp. 126-129.

CN201480041251.2 , "Notice of Decision to Grant", dated Jun. 22, 2017, 2 pages.

EP14846564.4 , "Extended European Search Report", dated May 11, 2017, 8 pages.

* cited by examiner

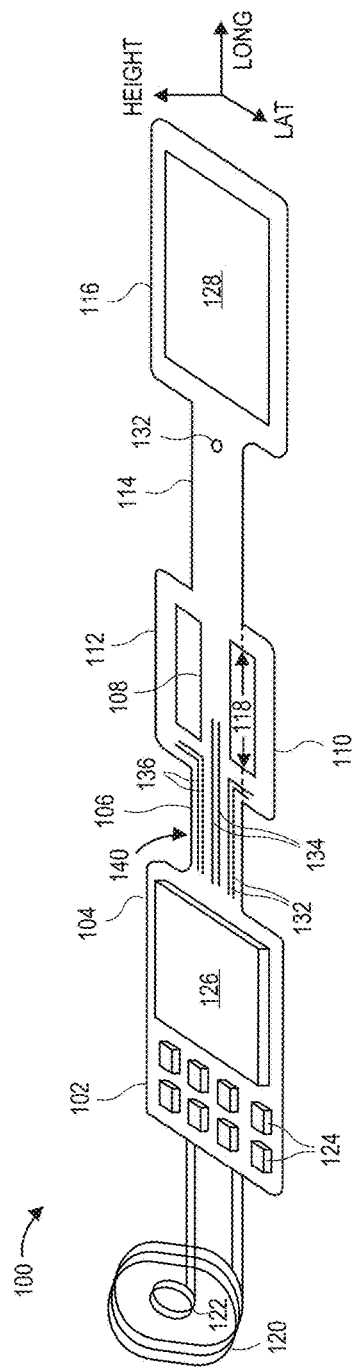
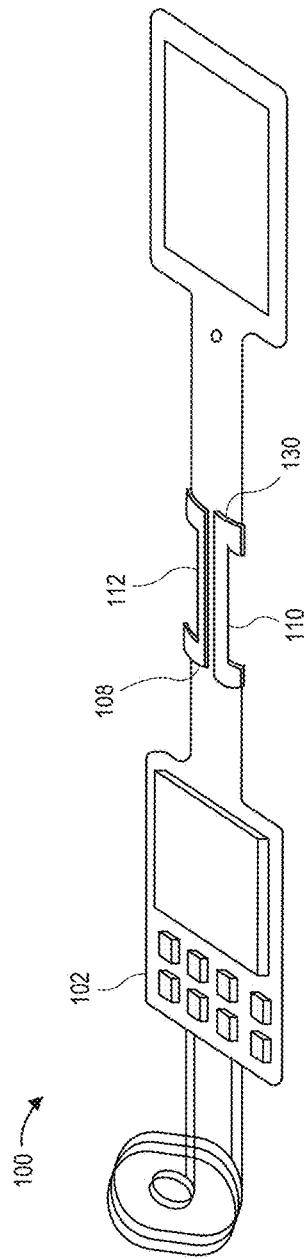

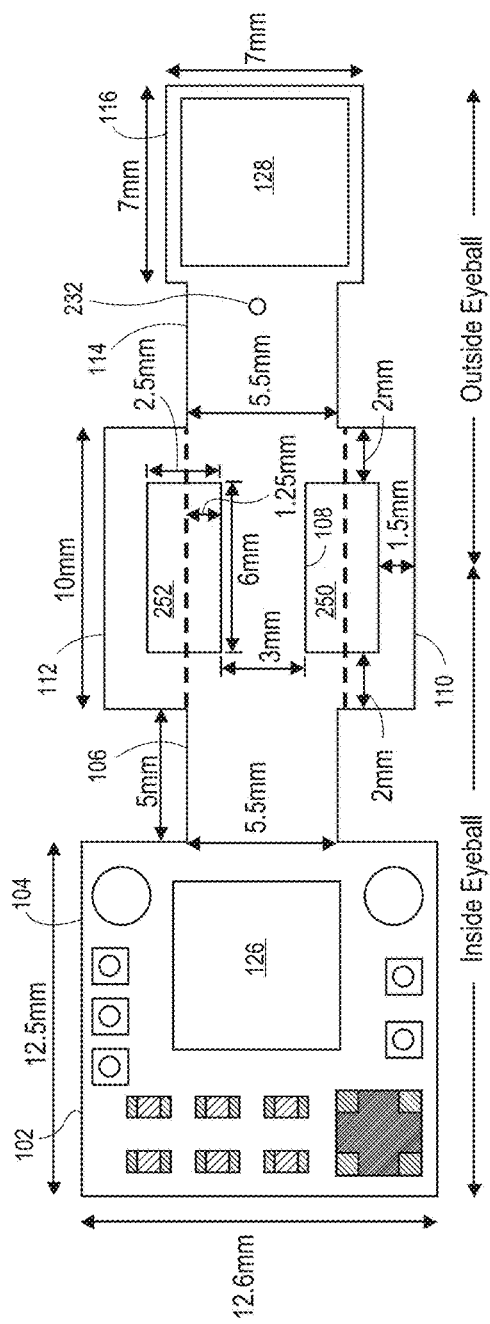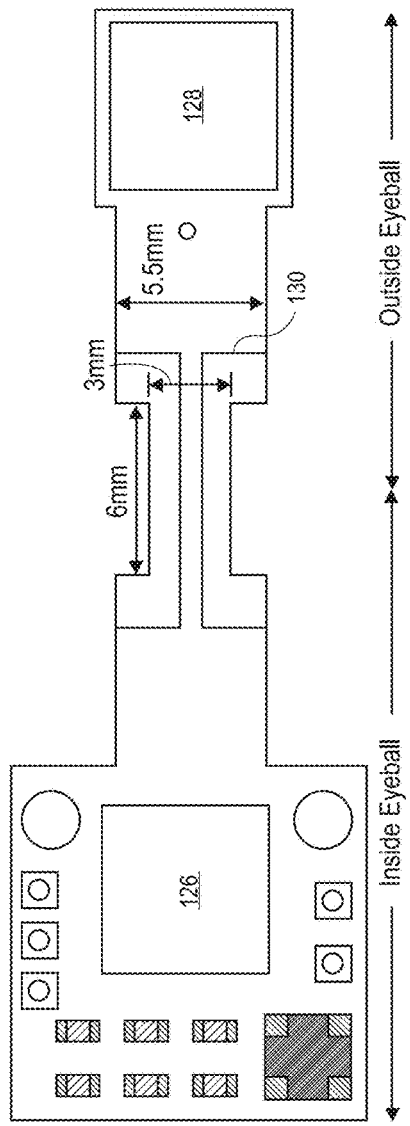
FIG. 2A
FIG. 2B

BIOCOMPATIBLE RIBBON CABLE WITH NARROW FOLDED SECTION

CROSS-REFERENCES TO RELATED APPLICATIONS

This application is a (bypass) continuation of International Application No. PCT/US2014/055462, filed Sep. 12, 2014, which claims the benefit of U.S. Provisional Patent Application No. 61/878,988, filed Sep. 17, 2013, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under EEC0310723 awarded by the National Science Foundation. The government has certain rights in the invention.

BACKGROUND

1. Field of the Art

Embodiments of the present invention generally relate to surgically implanted electronics, in particular, to a ribbon cable that runs through narrow slits in membranes such as the sclera of an eyeball.

2. Description of the Related Art

Age-related macular degeneration (AMD) and retinitis pigmentosa (RP) are two most common outer-retina degenerative diseases of the human eye. There is promise in the use of retinal prostheses in order to allow people afflicted with the diseases to see. Retinal prostheses, which bypass the defective outer-retina photoreceptors and electrically stimulate the inner-retina neurons directly, have allowed some blind people with AMD and RP to perceive light.

It is recognized that these early prostheses only involve a very small number of stimulating electrodes on the neurons. To realize facial recognition or large-sized letter reading, next-generation retinal prosthetic devices may use 1024 or more stimulating electrodes. A 1024-electrode implant can be configured as a 32-by-32 square array of electrodes or with different numbers of electrodes in rectangular, circular, or other shapes.

Around the world, much effort has been put to develop high-density multi-electrode arrays for retinal prosthetic applications. However, even the most advanced prostheses at this time do not have enough stimulating electrodes to restore vision to the desirable functional capability. The simulation results of facial recognition imply that a 1024-electrode retinal implant, with a corresponding number of channels, may be a minimum requirement for blind people to distinguish one from the other.

Stimulating such a large number of electrodes in parallel presents an engineering challenge considering constraints posed by an eyeball. Size, power, heat dissipation, and even buoyancy of electronics are among factors that affect design. Outside the eyeball, an integrated circuit (IC) chip that stimulates the electrodes is less constrained, but getting a thousand plus electrical signals from outside of the eyeball to inside the eyeball—in parallel—is a challenge.

From a surgical point of view, the size of an incision in the sclera of an eye is limited to 3 millimeters (mm) in order to maintain the eyeball's ocular integrity and avoid severe bleeding or inducing retinal detachment. Given a 3-mm wide opening, running 1024 wires in a 3-mm wide flat cable would require a 3-micron (μm) pitch for the wire traces. Pitch includes the width of each conductor (e.g., 1.5 μm) and the width of the gap or insulator between the conductors (e.g., 1.5 μm). Current manufacturing methods have trouble laying down adequate wire traces at a 3-micron pitch on biocompatible polymers such as parylene. And generally, the larger the width of the lines, the more reliably they can be manufactured.

There is a need in the art for improved electronics for surgical implantation.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

BRIEF SUMMARY

Generally, a biocompatible ribbon cable with one or more central 'wings' that can be laterally folded inward to narrow the central portion is described. The folded portion is narrow enough that a surgeon can fit it through a specified-width incision in a membrane, such as a sclera of an eyeball.

The ribbon cable can have an integrally formed electrode array and/or be attached to operative electronics, such as an electrode-stimulating IC chip, power and data coils (for inductive communication with external devices), and other components. The electrode array can be curved to match the curvature of a retina.

If there is more than one wing on the ribbon cable, the wings can be folded into the center such that they do not overlap, over each other so that they do overlap, over and under the central portion, or as otherwise needed for surgery. In any configuration, the resulting structure formed by a wing folded over another portion of the cable can be called a "stack."

The ribbon cable can be manufactured using microfabrication techniques, including chemical vapor deposition (CVD), photoresist masking and exposure, and chemical etching. It may or may not include a groove or other structure to assist in folding the wings.

Some embodiments of the present invention are related to a ribbon cable apparatus for connecting through a membrane. The apparatus includes a first ribbon cable portion, a second ribbon cable portion, a central ribbon cable portion supporting a first subset of electrical conductors extending between the first and second ribbon cable portions, the central ribbon cable portion being narrower than each of the first and second ribbon cable portions, a bypass ribbon cable portion supporting a second subset of electrical conductors extending between the first and second ribbon cable portions, the bypass ribbon cable portion being narrower than each of the first and second ribbon cable portions, the bypass ribbon cable portion diverging laterally from the central ribbon cable portion and being folded over the central ribbon cable portion into a stack such that the stack is narrower than the first and second ribbon cable portions.

Folding a structure "over" another structure includes folding them together in any orientation with respect to gravity. That is, the term "over" is not limited to one portion being greater in height than another portion.

The bypass ribbon cable portion may be a first bypass ribbon cable portion, and the apparatus can further include a second bypass ribbon cable portion supporting a third subset of embedded conductors extending between the first and second ribbon cable portions, the second bypass portion being narrower than the first and second ribbon cable portions, the second bypass ribbon cable portion diverging laterally from the central ribbon cable portion and being folded over or under the central ribbon cable portion into the stack. The second bypass ribbon cable portion can be folded under the central portion, thereby being opposite the first bypass portion.

The bypass portion can have a longitudinal crease therethrough. The bypass ribbon cable portion can be D- or U-shaped, A- or V-shaped, or as otherwise appropriate. The first and second subsets of electrical conductors can be embedded within a biocompatible polymer.

The apparatus can include an electrode array having electrodes configured to stimulate retinal ganglion cells within an eyeball, the electrode array being integrally formed with the second ribbon cable portion and connected with the first and second subsets of electrical conductors, and an integrated circuit connected with the electrical conductors of the first ribbon cable portion, the integrated circuit configured to send electrical pulses to the electrode array. The stack can be equal to or less than 3 millimeters wide. The electrode array can be about 7 mm by 7 mm square. "About" can mean within tolerances of ±1%, ±2%, ±3%, ±4%, ±5%, ±8%, ±10%, ±20%, ±25%, or as otherwise appropriate in the art for the structure at issue. The apparatus can include one or more electromagnetic inductor coils connected with the integrated circuit. The electrode array can include a spherically curved portion.

The ribbon cable portions can be integrally formed from parylene, polyimide, or other polymers. The ribbon cable portions can include two or more etched conductor layers. Any of the various embodiments may or may not be implanted into a subject.

Some embodiments are related to a ribbon cable apparatus for connecting through a membrane. The apparatus includes a ribbon cable having an aperture integrally formed therethrough, an electrical conductor passing on one side of the aperture and another electrical conductor passing on another side of the aperture, the ribbon cable being laterally folded over into a stack with a longitudinal crease through the aperture such that a portion of the folded-over ribbon cable proximate the aperture is narrower than a portion of the folded-over ribbon cable not proximate to the aperture.

The aperture may be a first aperture, the ribbon cable having an integrally formed second aperture lateral to the first aperture, the ribbon cable having a second longitudinal crease through the second aperture, the ribbon cable being laterally folded over or under into the stack. The apparatus can further include an electrode array having electrodes configured to stimulate retinal ganglion cells within an eyeball, the electrode array being integrally formed with a first end portion of the ribbon cable and connected with the electrical conductor, and an integrated circuit connected with electrical conductors of a second end portion of the ribbon cable, the integrated circuit configured to send electrical pulses to the electrode array.

Some embodiments are related to a method of manufacturing an apparatus for connecting through a membrane. The method can include forming a biocompatible ribbon cable using chemical vapor deposition, photoresist application, and etching, the ribbon cable having a bypass portion that splits from a center portion of the ribbon cable to define an aperture through the ribbon cable, and folding, along a line through the aperture, the bypass portion over the center portion to form a stack such that the stack of the center and bypass portions is narrower than another portion of the ribbon cable.

The bypass portion may be a first bypass portion and the aperture may be a first aperture, the ribbon cable having a second bypass portion, the second bypass portion defining a second aperture lateral to the first aperture through the ribbon cable, the method further including folding, along a second line through the second aperture, the second bypass portion over or under the center portion into the stack.

The second bypass portion can be folded under the central portion, thereby being folded opposite the first bypass portion. The method can include creasing the bypass portion through the line through the aperture. The method can include placing an electrode array on an end of the ribbon cable into a spherical mold, and heating the electrode array sufficient to impart permanent curvature to the electrode array. The method can include inserting the folded stack through a slit in a membrane. The membrane can be a sclera of an eyeball.

A further understanding of the nature and the advantages of the embodiments disclosed and suggested herein may be realized by reference to the remaining portions of the specification and the attached drawings.

BRIEF DESCRIPTION OF THE DRAWINGS

FIG. 1A is a perspective illustration of an unfolded ribbon cable in accordance with an embodiment.

FIG. 1B is a perspective illustration of the ribbon cable of FIG. 1A in a folded configuration.

FIG. 2A is a plan view illustration of an unfolded ribbon cable of FIG. 1A.

FIG. 2B is a plan view illustration of the folded ribbon cable of FIG. 1B.

Figure 3:
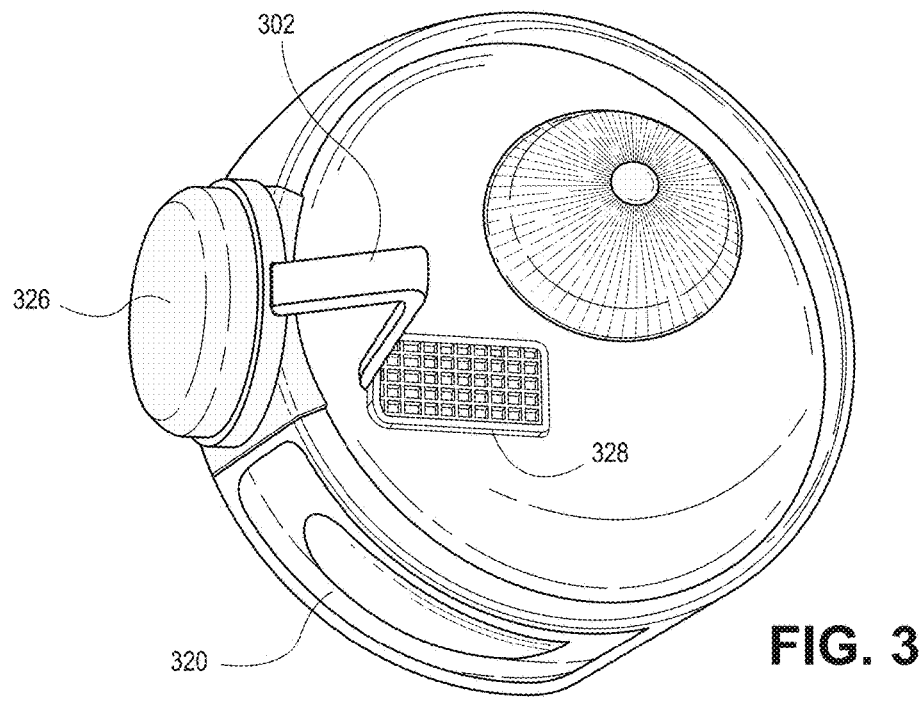
FIG. 3 illustrates implantation of a ribbon cable in and around an eyeball in accordance with an embodiment.

Reference to the remaining portions of the specification, including the drawings and claims, will realize other features and advantages of the present invention. Further features and advantages of the present invention, as well as the structure and operation of various embodiments of the present invention, are described in detail below with respect

DETAILED DESCRIPTION

A 1024-channel retinal IC chip has been designed and functionalized with six capacitors and one oscillator. In order to connect the IC chip's conductive pads with retinal ganglion cells within an eyeball, the chip is integrated with a parylene, flexible ribbon cable with an integrated electrode and implant inside an eyeball.

The ribbon cable includes a first wide portion and a second wide portion connected by a central bridge portion and at least one bypass 'wing' portion. The ribbon cable has a set of electrical traces (conductors) that individually run between the first wide portion and the second wide portion. For example, a single conductive pad in the first portion is connected by an electrical conductor to a single electrode in the second portion.

A first subset of electrical conductors extends between the first and second wide portions via the central portion. A second subset of electrical conductors extends between the first and second wide portions via one of the bypass portions. A third subset of electrical conductors can extend between the first and second wide portions via one of the other bypass portions.

The wings can be folded laterally over the central portion so that the folded, stacked portion is narrower than the wide portions.

Technical advantages of some of the embodiments include that the narrower, stacked portion of the ribbon cable can fit through narrower incisions when implanting in a subject's body than the rest of the cable. For example, the narrow portion of a ribbon cable can slip through a 3 mm wide incision in a sclera. Yet the 'narrower' portion can carry just as many independent signals as the wider portions of the cable and maintain an adequate pitch (i.e., the pattern spacing of traces). The minimum size of features may be dictated by manufacturing, materials, or otherwise, and stacking portions of the ribbon cable by folding them effectively gives more room for those features to be laid out on the ribbon cable.

FIG. 1A is a perspective illustration of an unfolded ribbon cable in accordance with an embodiment. System 100 includes ribbon cable 102, which has a portion 104 on which IC chip 126 is connected. Capacitors 124, power coil 120, and data coil 122 are connected to IC chip 126 by electrical traces embedded in ribbon cable portion 104.

Ribbon cable 102 has first wide ribbon cable portion 106 and second wide portion 114. The first and second portions 106 and 114 have a set of conductors 140 that are connected to each other. First subset 134 of set of conductors 140 traverses central narrow ribbon cable portion 108. Second subset 132 of set of conductors 140 traverses first bypass ribbon cable portion 110. Third subset 136 of set of conductors 140 traverses second bypass ribbon cable portion 112.

Ribbon cable 102 has portion 116 into which electrode array 128 is integrally formed.

"Integrally formed" parts include those that are deposited, etched, cured, or formed at the same time as one another such that the result is that they are connected by a common material with one another, or as otherwise known in the art.

A "longitudinal" direction on a ribbon cable is a direction of longest measurements of the cable, or as otherwise known in the art. For example, a longitudinal direction in the figure is one running between portions 104 and 116 of the exemplary ribbon cable.

A "lateral" direction on a ribbon cable is a direction perpendicular to the longitudinal direction and within the plane of the ribbon cable, or as otherwise known in the art. For example, a lateral direction in the figure is one running from a far side of the cable (in the page) to a near side.

A "height" of a ribbon cable includes a direction of smallest dimensions, or as otherwise known in the art. For example, a height of the ribbon cable in the figure is one running vertically in the plane of the page.

A "ribbon cable" includes any cable having a flattened portion with conductors running side by side in the flattened portion, or as otherwise known in the art. A ribbon cable may be micro-fabricated or constructed using classical methods.

FIG. 1B is a perspective illustration of the ribbon cable of FIG. 1A in a folded configuration. First bypass ribbon cable portion has been folded laterally through longitudinal crease line 118 over central ribbon cable portion 108, and second bypass ribbon cable portion has been folded laterally over central ribbon cable portion 108. In the exemplary embodiment, bypass ribbon cable portions meet edge-to-edge in approximately the center of central ribbon cable portion 108. The bypass ribbon cable portions form stack 130 with central ribbon cable portion 108.

In the exemplary embodiment, two bypass wings are incorporated into the design in order to relax the pitch density of conductors. After folding and fixing the wings 110 and 112 to central portion 108 by epoxy, the interconnection area becomes 3 mm wide and 6 mm long. This can satisfy the incision limitation for structural integrity of the eyeball and supply some freedom during implantation.

Retinal tack aperture 132 is used during surgery to affix electrode array 128 to the retina.

FIGS. 2A-2B are plan view illustrations of the unfolded and folded ribbon cable of FIGS. 1A-1B, respectively. Dimensions in this paragraph as given as longitudinal first followed by lateral, unless otherwise specified. Portion 104 of ribbon cable 102 is 12.5 mm by 12.6 mm. First portion 106 is 5 mm by 5.5 mm. Central portion 108 is 6 mm by 3 mm. Second portion 114 has a lateral measurement of 5.5 mm. Portion 116, with electrode array 128, is 7 mm by 7 mm.

Bypass portions 110 and 112 each diverge laterally from the central ribbon cable portion 2.75 mm and run longitudinally a total (i.e., at their maximum extents) of 10 mm between first and second portions 106 and 114. The paths of bypass portions 110 and 112 are 2 mm wide (longitudinally) in the legs and 1.5 mm wide (laterally) in the section that is parallel to central portion 108.

Aperture 250 is created or otherwise defined through ribbon cable 102 using micromachining techniques, such as etching around developed photoresist. Bypass portion 110 carries at least one conductor that passes on one side of aperture 250, while central portion 108 carries at least one conductor that passes on another side of aperture 250. Similarly, bypass portion 112 carries at least one conductor that passes on one side of aperture 252, while central portion 108 carries another on the other side of aperture 252.

Bypass portions 110 and 112 are D- or U-shaped. In some embodiments, the bypass portions diagonally meet at a sharp point, reflecting an A- or V-shape.

After folding up bypass portions 110 and 112 over central portion 108 (see FIG. 2B), stack 130 forms a narrow neck that is 6 mm (long) and only 3 mm wide.

FIG. 3 illustrates implantation of a ribbon cable in and around an eyeball in accordance with an embodiment. Parylene ribbon cable 302 penetrates through the eye wall, allowing electrode array 328 to stimulate the retina, specifically stimulating retinal ganglion cells within the eyeball. Application-specific integrated circuit (ASIC) 326 and receiver coil 320 are sutured between the conjunctiva and eyelid.

Figure 4:
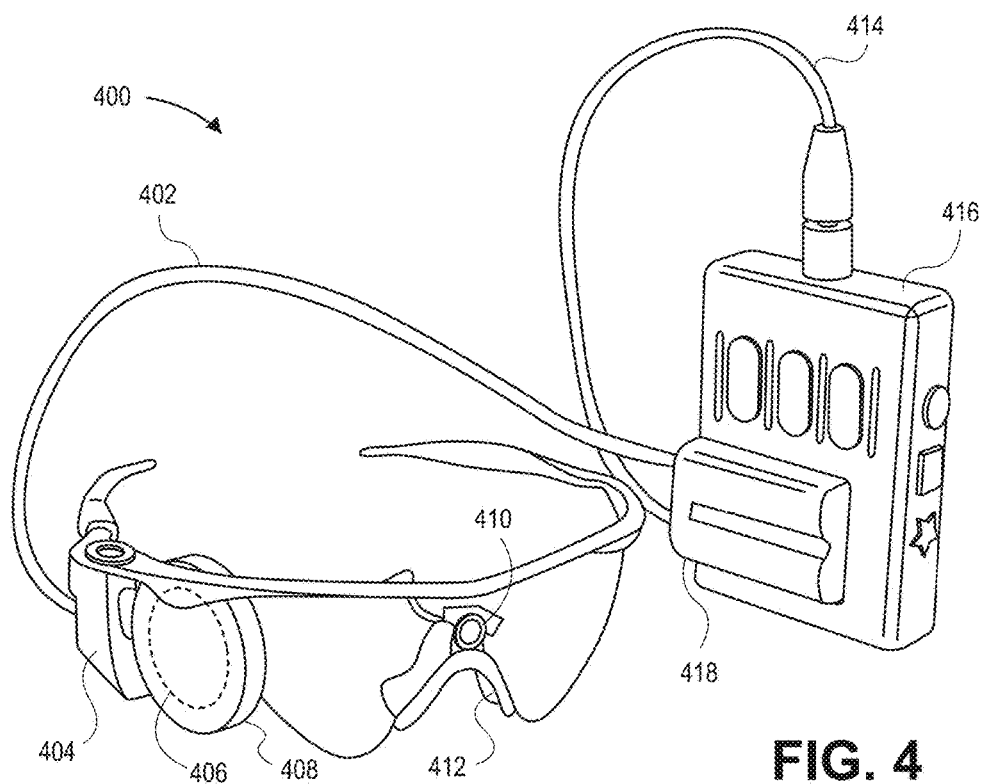
FIG. 4 illustrates a wearable transmitter assembly in accordance with an embodiment.

FIG. 4 illustrates a wearable transmitter assembly in accordance with an embodiment.

External unit 400 includes transmitter coil 406 housed in transmitter assembly 408. Transmitter assembly 408 is positioned to the side of a user's eye by glasses 412. Other positioning means besides glasses are envisioned.

Glasses 412 hold miniature camera 410 and video processor 404, which are connected by cable 402 to adaptor 418. Cable 414 connects another port of adaptor 418 to battery pack 416, which can be worn on a belt.

Figure 5B:
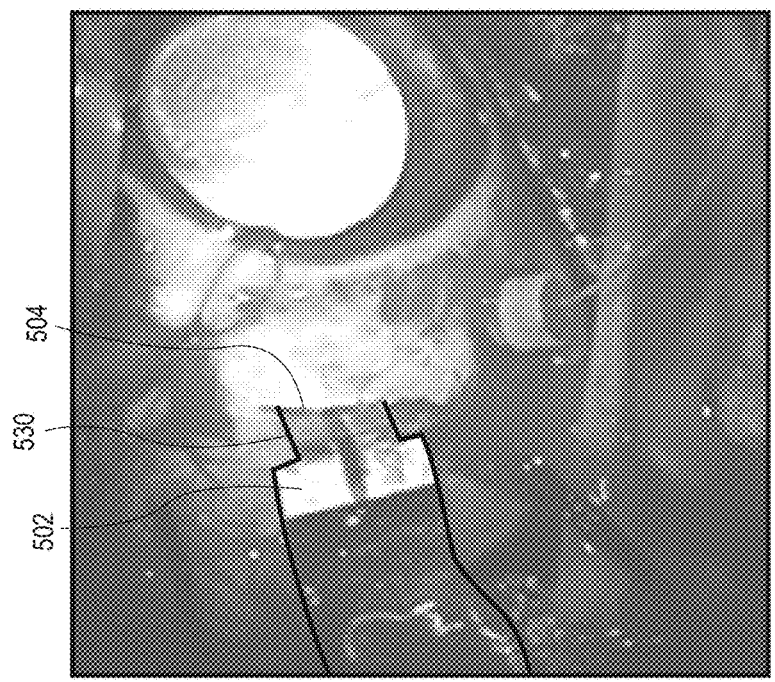
FIG. 5B is an image of the folded, narrower portion of a ribbon cable extending through an incision in any eyeball in accordance with an embodiment.
Figure 5A:
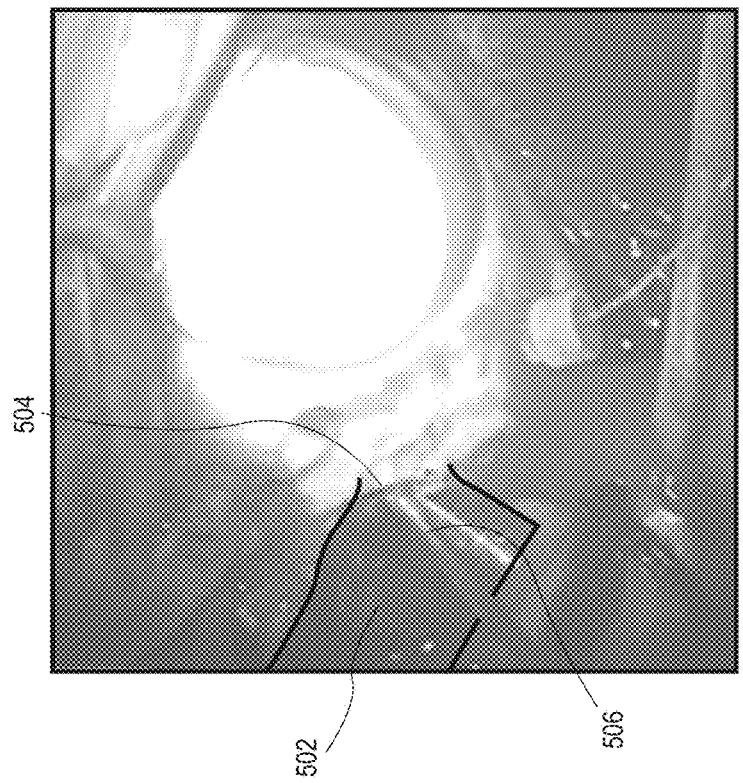
FIG. 5A is an image of an end of the ribbon cable being inserted to an incision in an eyeball accordance with an embodiment.

FIG. 5A is an image of an end of the ribbon cable being inserted to an incision in an eyeball accordance with an embodiment. The electrode array end of ribbon cable 502 is started into incision 504 using surgical tool 506. During surgery, a surgeon may carefully curl or bend the ribbon cable and electrodes in order to temporarily fit them through the incision.

FIG. 5B is an image of the folded, narrower portion of a ribbon cable extending through an incision in any eyeball in accordance with an embodiment. Narrow stack portion 530 of ribbon cable 502 extends through incision 504 with room to spare. Ideally, the sclera will heal and seal the ribbon cable in this position.

Figure 6:
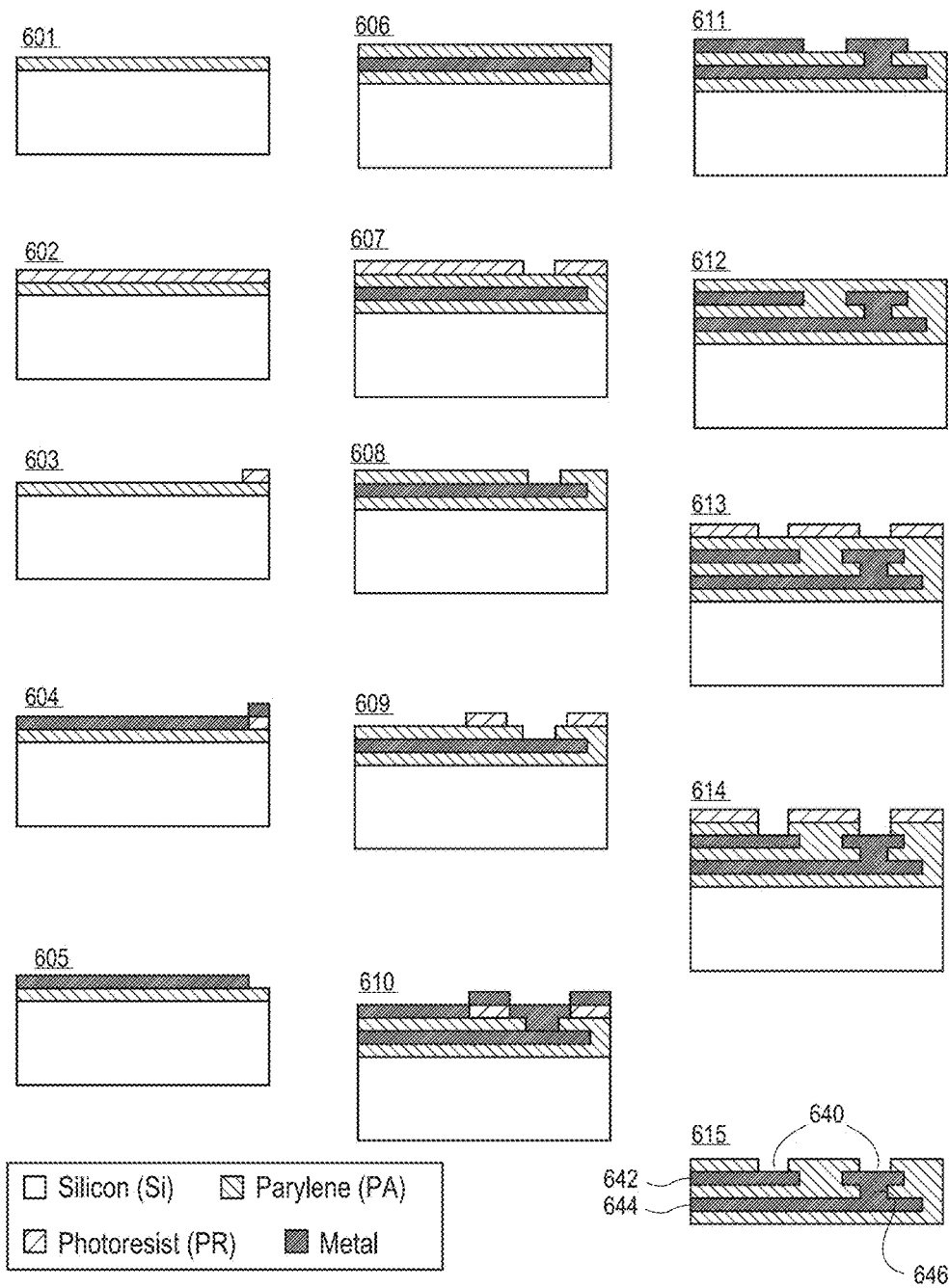
FIG. 6 shows a micro-fabrication process for a dual-layered ribbon cable in accordance with an embodiment.

FIG. 6 shows a micro-fabrication process for a dual-layered ribbon cable in accordance with an embodiment.

In operation 601, parylene is deposited by chemical vapor deposition (CVD) on a silicone substrate. In operation 602, photoresist is spun into a thin layer over the parylene. In operation 603, the photoresist is exposed, developed, and removed. In operation 604, a first metal is evaporated and deposited over the parylene and remaining photoresist. In operation 605, the photoresist is removed in order to remove the metal deposited over it.

In operation 606, a second layer of parylene is deposited. In operation 607, more photoresist is spun into a fine layer, exposed, developed, and removed. In operation 608, vias are etched, and photoresist is then removed. In operation 609, more photoresist is spun into a thin layer, exposed, developed, and removed. In operation 610, a second metal is evaporated and deposited over the second layer of parylene.

In operation 611, the remaining photoresist, and any metal on top of it, is stripped. In operation 612, a third layer of parylene is deposited. In operation 613, more photoresist is spun into a fine layer, exposed, and developed. In operation 614, the third layer of parylene is etched where exposed.

In operation 615, the photoresist is stripped, and the layered ribbon cable assembly is released from the silicon substrate. Each conductive pad 640 is connected to metal traces embedded within the ribbon cable. Dual metal layers, including first metal layer 642 and second metal layer 644, effectively double the amount of conductors that can fit into the width of the ribbon cable. Each second layer 644 conductor is connected through a respective via 646 to a respective conductive pad.

In some embodiments, polyimide or other biocompatible polymers are used instead of or in addition to the biocompatible polymer parylene.

"Biocompatible" materials include those that have been determined by a government agency to avoid corrosion by bodily fluids for extended periods as well as be nontoxic. Titanium, gold, parylene, and polyimide are among the many biocompatible materials available for use in humans. For example, parylene has demonstrated bio-compatibility as a United States Pharmacopeial Convention (USP) Class VI biocompatible polymer.

Figure 7:
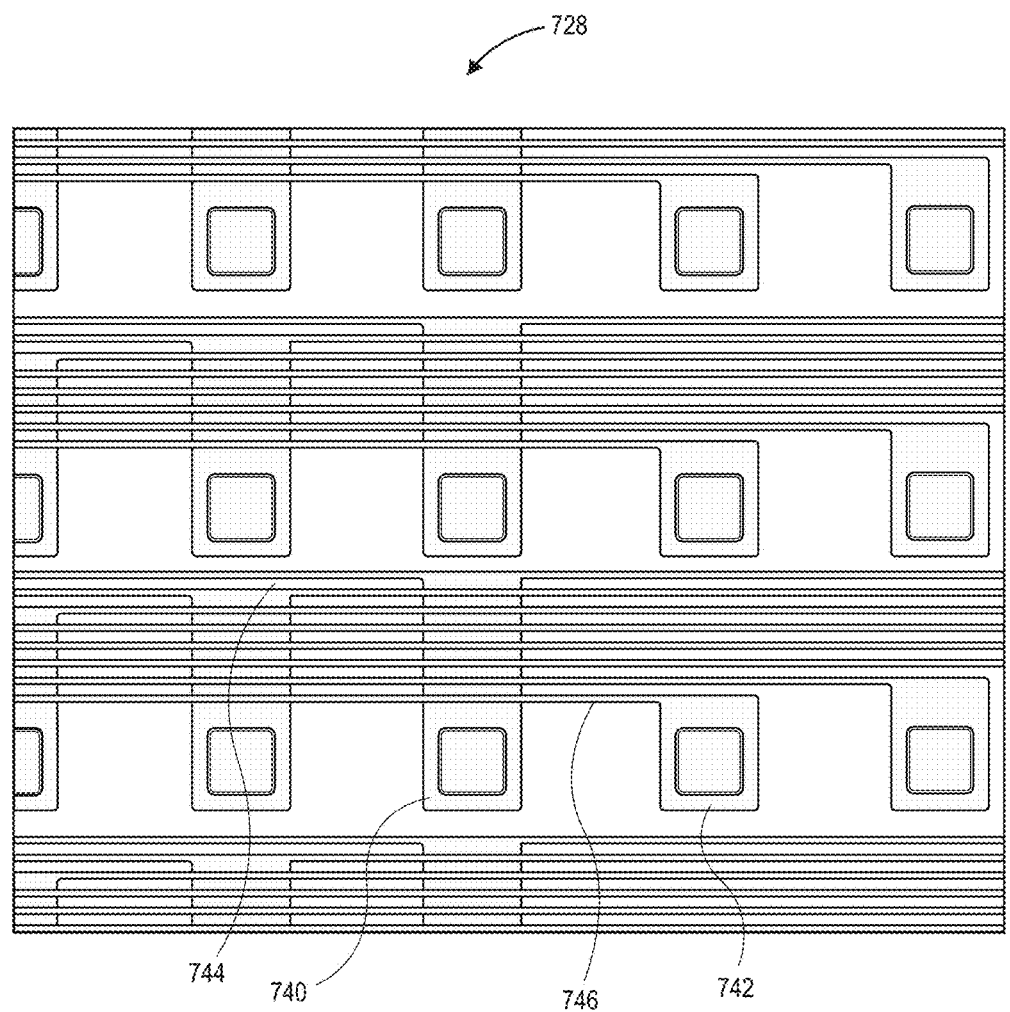
FIG. 7 illustrates a close-up view of a dual metal layer electrode array in accordance with an embodiment.

FIG. 7 illustrates a close-up, top down view of a dual metal layer electrode array in accordance with an embodiment. In electrode array 728, conductive pad 740 is connected through a via to bottom layer traces 744, which run underneath top layer traces 746. Conductive pad 742 is connected to top layer trace 746.

Figure 8:
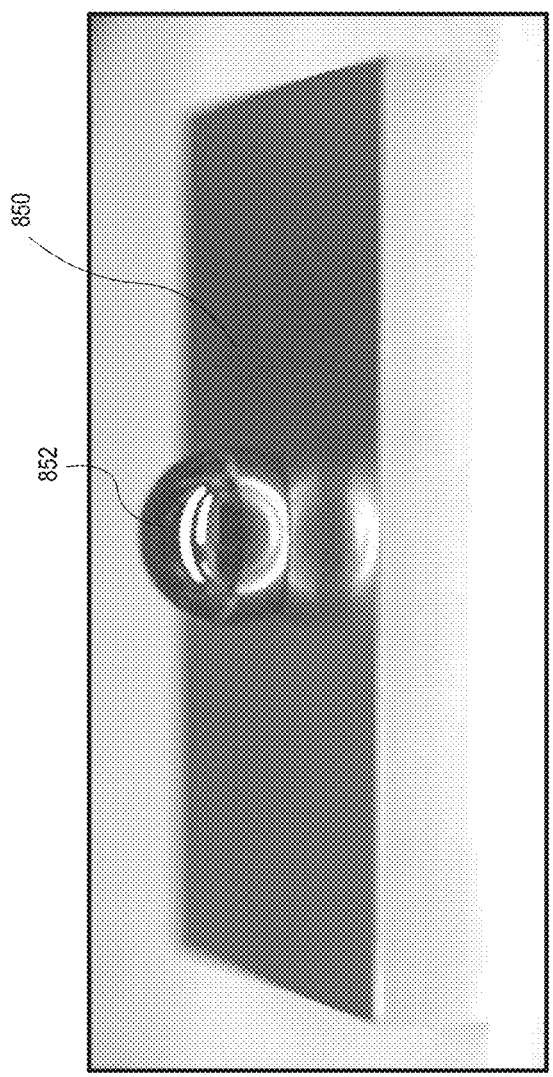
FIG. 8 is an image of a mold for imparting curvature to an electrode array in accordance with an embodiment.

FIG. 8 is an image of a mold for imparting curvature to an electrode array in accordance with an embodiment. With a correct curvature design, an electrode array can be better attached to the retinal tissue, which is beneficial for stimulation. A parylene-based electrode array can be spherically curved by thermoforming at temperature higher than its glass transition temperature using a 6061 aluminum mold 850 comprising a recessed concave region and mating stainless steel sphere ball 852 that approximates the curvature of the retina.

Figure 9:
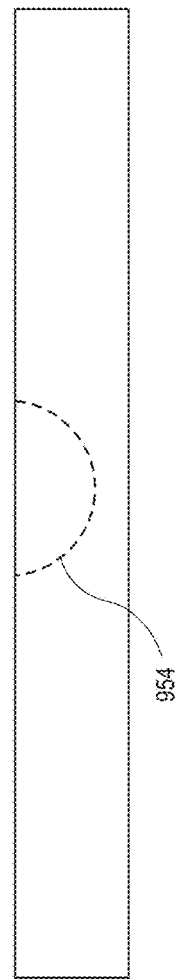
FIG. 9 is an elevation view illustration of the mold shown in FIG. 8.

FIG. 9 is an elevation view illustration of the mold shown in FIG. 8, showing recessed concave region 954. For canine-size retinas for testing, the radius is 11.1 mm (0.438 inches).

Figure 10:
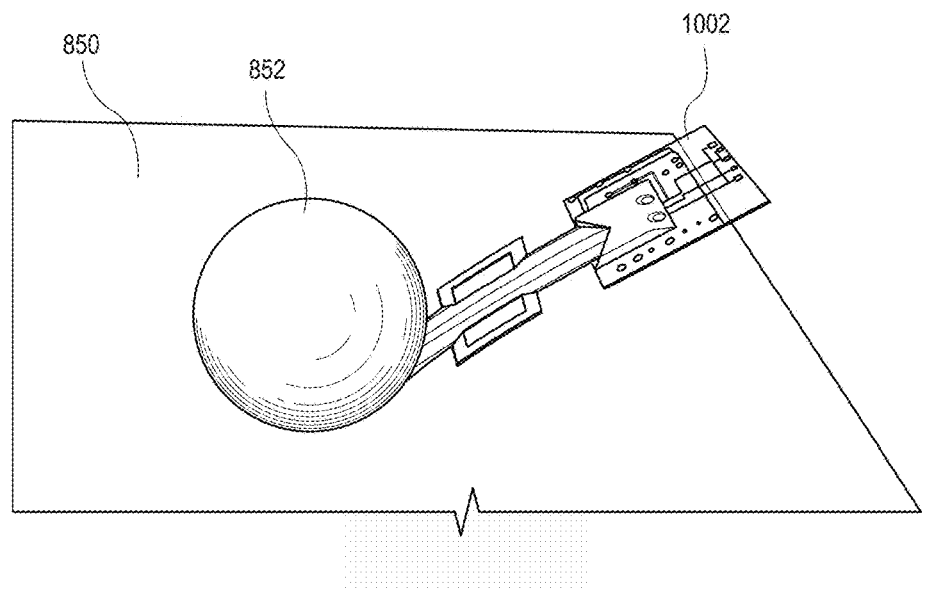
FIG. 10 illustrates an electrode array within the mold of FIG. 8.
Figure 11:
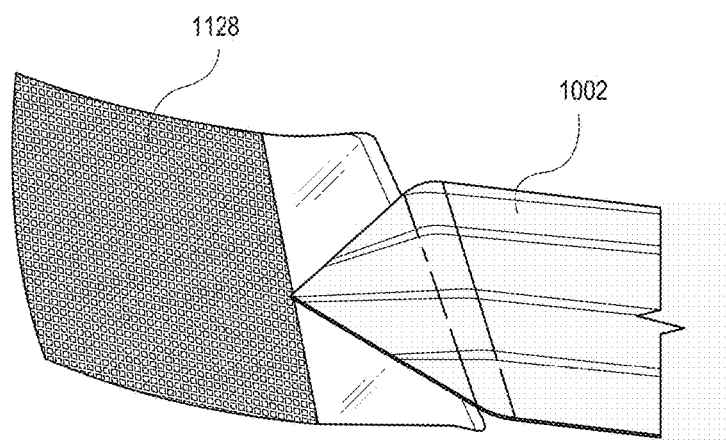
FIG. 11 illustrates an electrode array imparted spherical curvature from the mold of FIG. 8.

FIG. 10 illustrates an electrode array within the mold 850, and FIG. 11 illustrates an electrode array imparted spherical (in two dimensions) curvature. Electrode array 1128 of ribbon cable 1002 is placed into spherical mold 850 with ball 852 resting atop it. It is heated past parylene's glass transition temperature, at approximately 200° C. for 2 days in a vacuum oven with nitrogen backfill to permanently form the spherically curved electrode array. The resulting product is sterilized using ethylene oxide gas.

Figure 12:
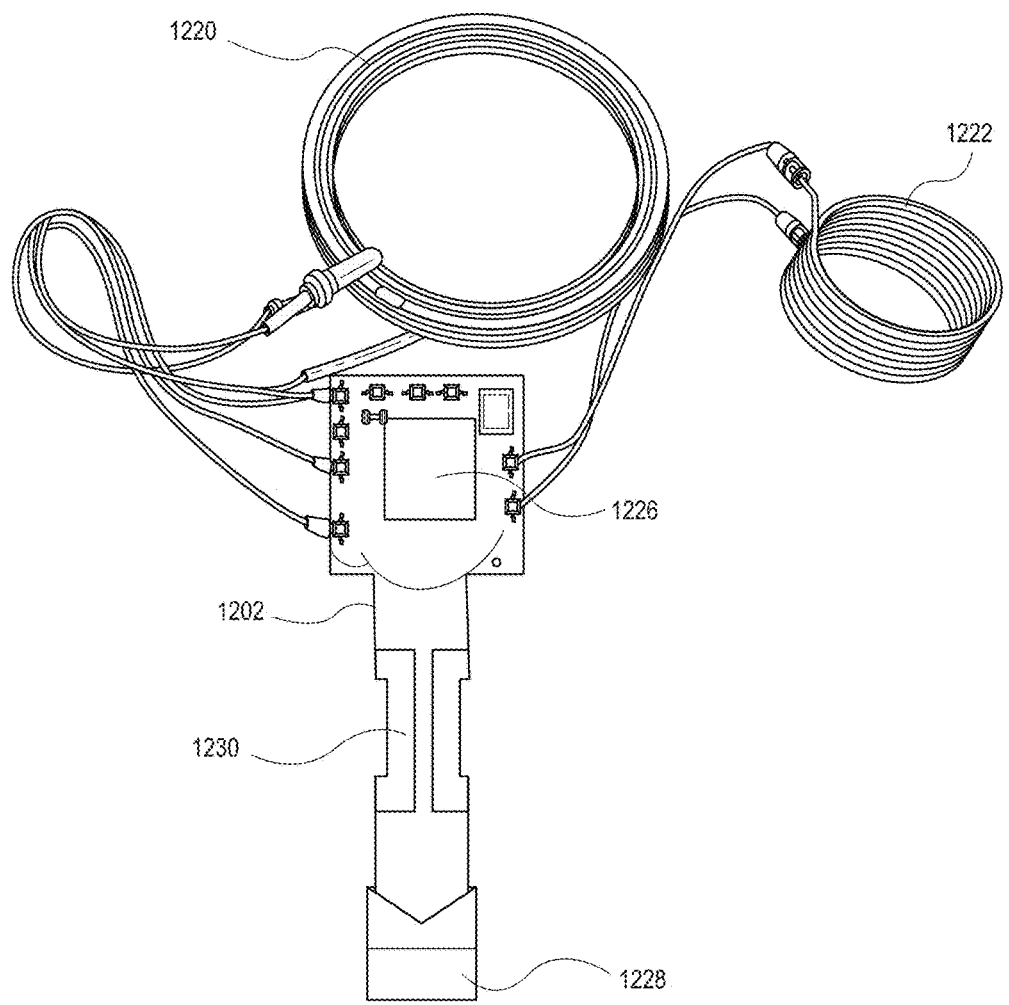
FIG. 12 illustrates a retinal implant apparatus with coils in accordance with an embodiment.

FIG. 12 illustrates a retinal implant apparatus with coils in accordance with an embodiment. Ribbon cable 1202 has IC 1226, power coil 1220, and data coil 1222 attached on one end. On the other end of ribbon cable 1202 is integrally formed electrode 1228. Between the two ends is narrow stacked portion 1230 of ribbon cable 1202. The narrow portion can fit through narrow incisions.

Although the ribbon cable apparatus has been described for interocular implants, embodiments of the invention can be used for other medical devices that require a cable to pierce through a membrane.

Figure 13:
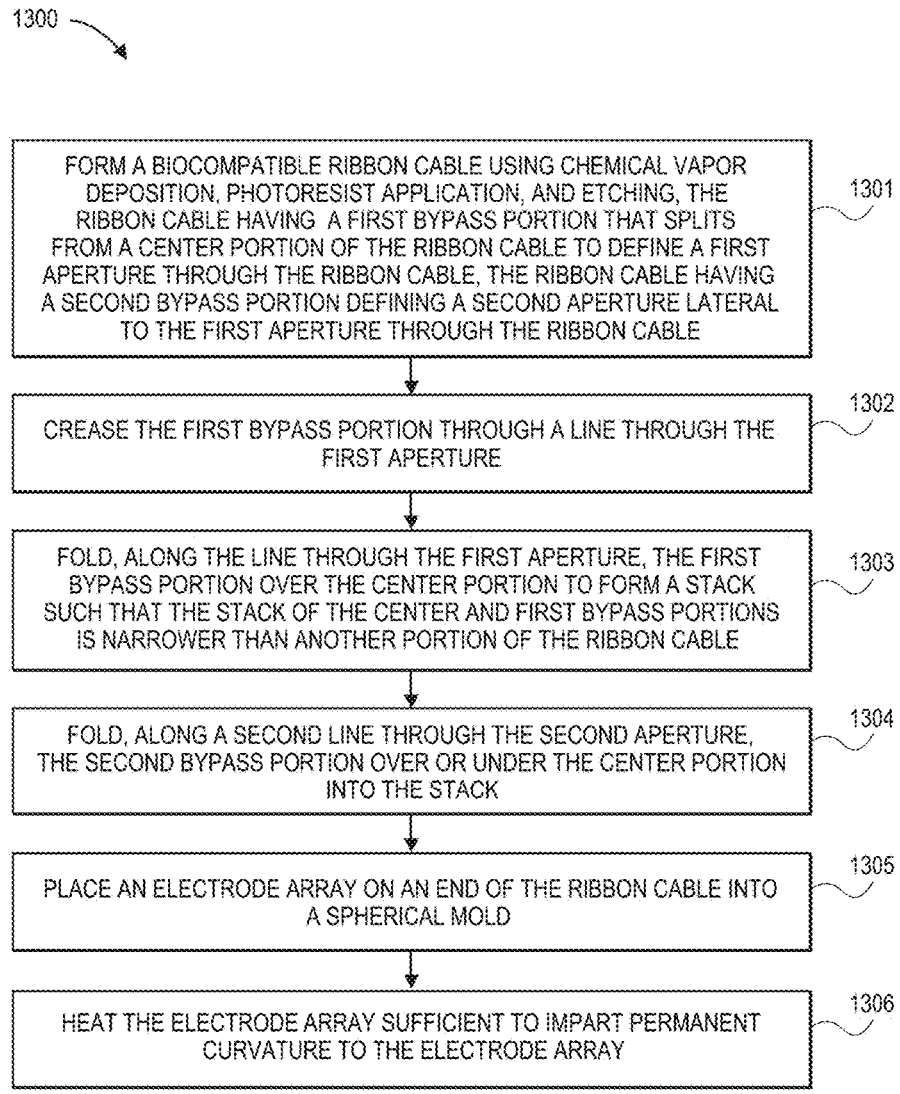
FIG. 13 is a flowchart of a process in accordance with an embodiment.

FIG. 13 is a flowchart of process 1300 in accordance with an embodiment. In operation 1301, a biocompatible ribbon cable is formed using chemical vapor deposition (CVD), photoresist application, and etching, the ribbon cable having a first bypass portion that splits from a center portion of the ribbon cable to define a first aperture through the ribbon cable. The ribbon cable also has a second bypass portion defining a second aperture lateral to the first aperture through the ribbon cable. In operation 1302, the first bypass portion is creased through a line through the first aperture. In operation 1303, the first bypass portion is folded along the line through the first aperture and over the center portion to form a stack such that the stack of the center and first bypass portions is narrower than another portion of the ribbon cable. In operation 1304, the second bypass portion is folded along a second line through the second aperture over (or under) the center portion into the stack. In operation 1305, an electrode array is placed on an end of the ribbon cable into a spherical mold. In operation 1306, the electrode array is heated within the spherical mode sufficiently to impart a permanent curvature to the electrode array.

The invention has been described with reference to various specific and illustrative embodiments. However, it should be understood that many variations and modifications may be made while remaining within the spirit and scope of the following claims.

What is claimed is:

1. A ribbon cable apparatus configured for implantation into a subject, the apparatus comprising:
   a ribbon cable having:
      a first aperture integrally formed therethrough, an electrical conductor passing on one side of the first aperture and another electrical conductor passing on another side of the first aperture, the ribbon cable being laterally folded over into a stack with a longitudinal crease through the first aperture; and
      a second aperture integrally formed through the ribbon cable and lateral to the first aperture, the ribbon cable having a second longitudinal crease through the second aperture, the ribbon cable being laterally folded over or under the stack along the second longitudinal crease,
   wherein a portion of the folded-over ribbon cable between the apertures is narrower than a portion of the folded-over ribbon cable not between the apertures.

2. The apparatus of claim 1 further comprising:
   an electrode array having electrodes configured to stimulate retinal ganglion cells within an eyeball, the electrode array being integrally formed with a first end portion of the ribbon cable and connected with the electrical conductors; and
   an integrated circuit connected with electrical conductors of a second end portion of the ribbon cable, the integrated circuit configured to send electrical pulses to the electrode array.

3. The apparatus of claim 2 wherein the electrode array is about 7 mm by 7 mm square.

4. The apparatus of claim 2 further comprising:
   at least one electromagnetic inductor coil connected with the integrated circuit.

5. The apparatus of claim 2 wherein the electrode array includes a spherically curved portion.

6. The apparatus of claim 1 wherein the ribbon cable on one side of the first aperture is folded over into the stack and the ribbon cable on one side of the second aperture is folded under the stack.

7. The apparatus of claim 1 wherein portions of the ribbon cable around the first and second apertures are D- or U-shaped.

8. The apparatus of claim 1 wherein portions of the ribbon cable around the first and second apertures are A- or V-shaped.

9. The apparatus of claim 1 wherein the electrical conductors are embedded within a biocompatible polymer.

10. The apparatus of claim 1 wherein the stack is equal to or less than 3 millimeters wide.

11. The apparatus of claim 1 wherein the ribbon cable is formed from parylene or polyimide.

12. The apparatus of claim 1 wherein the ribbon cable includes two or more etched conductor layers.

* * * * *